(12) United States Patent
Elaissari et al.

(10) Patent No.: US 7,700,744 B2
(45) Date of Patent: *Apr. 20, 2010

(54) METHOD FOR ISOLATING PROTEINS OR PROTEIN AND NUCLEIC ACID ASSOCIATIONS, OR PARTICLE AND PROTEIN COMPLEXES, REAGENT AND USES

(75) Inventors: Abdelhamid Elaissari, Lyons (FR); Bernard Mandrand, Villeurbanne (FR); Thierry Delair, Echalas (FR); Doran Spencer, Eureka, CA (US); Ahmed Arkis, Lyons (FR)

(73) Assignee: Biomerieux, Marcy l'Etoile (FR)

( * ) Notice: Subject to any disclaimer, the term of this patent is extended or adjusted under 35 U.S.C. 154(b) by 537 days.

This patent is subject to a terminal disclaimer.

(21) Appl. No.: 11/320,574

(22) Filed: Dec. 30, 2005

(65) Prior Publication Data
US 2006/0105326 A1    May 18, 2006

Related U.S. Application Data

(62) Division of application No. 10/182,126, filed as application No. PCT/FR01/00205 on Jan. 22, 2001, now Pat. No. 7,060,804.

(30) Foreign Application Priority Data
Jan. 21, 2000    (FR)    .................... 00 00862

(51) Int. Cl.
*A23J 1/00*    (2006.01)
(52) U.S. Cl. .................... 530/412; 530/300; 530/350; 435/7.1; 435/6; 435/345
(58) Field of Classification Search .................... None
See application file for complete search history.

(56) References Cited

U.S. PATENT DOCUMENTS

| 4,018,886 | A | * | 4/1977 | Giaever .................... 436/526 |
| 4,888,124 | A | | 12/1989 | Blum et al. |
| 5,049,469 | A | | 9/1991 | Pierce et al. |
| 5,051,469 | A | | 9/1991 | Udipi |
| 5,723,344 | A | | 3/1998 | Mabilat et al. |
| 5,756,273 | A | | 5/1998 | Wang et al. |
| 6,521,341 | B1 | | 2/2003 | Elaissari et al. |

FOREIGN PATENT DOCUMENTS

| EP | DE 198 03 098 A1 | 7/1999 |
| WO | WO 98/01482 | 1/1998 |
| WO | WO/ 99/35500 | 7/1999 |

OTHER PUBLICATIONS

V. Chalapati Rao, S.V. Waghmare, and S.B. Lakhe; "Detection of Viruses in Drinking Water by Concentration on Magnetic Iron Oxide"; Applied and Environmental Microbiology, vol. 42, No. 3, Sep. 1981, pp. 421-426.
Jonathan B. Katz et al.; "Colorimetric Diagnosis of Prolonged Bluetongue Viremia in Sheep, Using an Enzyme-Linked Oliogonucleotide Sorbent Assay of Amplified Viral Nucleic Acids"; Am J Vet Res, vol. 54, No. 12, Dec. 1993, pp. 2021-2026.
Francois Mallet et al.; "Enzyme-Linked Oligosorbent Assay for Detection of Polymerase Chain Reaction-Amplified Human Immunodeficiency Virus Type 1"; Journal of Clinical Microbiology, Jun. 1993, pp. 1444-1449.
Donald B. Smith et al.; "Discrimination of Hepatitis G Virus/GVB-C Geographical Variants by Analysis of the 5' Non-Coding Region", Journal of General Virology, vol. 78, 1997, pp. 1533-1542.
Berbert Morawetz and Walter L. Hughes, Jr.; "The Interaction of Proteins with Synthetic Polyelectrolytes. I. Complexing of Bovine Serum Albumin."; vol. 56, Aug. 1951, pp. 64-69.
Rao, Wei; Song, Hongtao; Yuan, Runzhang; "The Structure and Properties of Magnetic Microbeads"; 6001 Chemical Abstracts, XP-002152837; vol. 125, Nov. 18, 1996, No. 21.

* cited by examiner

*Primary Examiner*—Hope A Robinson
(74) *Attorney, Agent, or Firm*—Oliff & Berridge, PLC

(57) ABSTRACT

The magnetic colloidal particles comprise a core and an envelope in which the core is magnetic and is coated with at least one polymer comprising functional groups X chosen from amine, hydroxyl, thiol, aldehyde, ester, anhydride, acid chloride, carbonate, carbamate, isocyanate and isothiocyanate groups, or mixtures thereof, at least one fraction of which has reacted with other functional groups of the envelope, and the envelope comprises a polymer bearing ionizable functional groups, Z and Z', which may be identical or different, chosen from amine, carboxylic acid, ester, anhydride, aldehyde, thiol, disulfide, α-halocarbonyl, sulfonic acid, maleimide, isocyanate and isothiocyanate groups, which have partially reacted with the functional groups X of the core. These magnetic colloidal particles can be used to isolate biological material.

6 Claims, No Drawings

SEQUENCE LISTING

<160> NUMBER OF SEQ ID NOS: 16

<210> SEQ ID NO 1
<211> LENGTH: 18

```
<212> TYPE: DNA
<213> ORGANISM: Artificial Sequence
<220> FEATURE:
<223> OTHER INFORMATION: PCR primer

<400> SEQUENCE: 1
aggtgtggat gggtgatg                                              18

<210> SEQ ID NO 2
<211> LENGTH: 21
<212> TYPE: DNA
<213> ORGANISM: Artificial Sequence
<220> FEATURE:
<223> OTHER INFORMATION: PCR primer

<400> SEQUENCE: 2
atgccacccg ccctcacccg a                                          21

<210> SEQ ID NO 3
<211> LENGTH: 21
<212> TYPE: DNA
<213> ORGANISM: Artificial Sequence
<220> FEATURE:
<223> OTHER INFORMATION: PCR primer

<400> SEQUENCE: 3
ttggtaggtc gtaaatcccg g                                          21

<210> SEQ ID NO 4
<211> LENGTH: 24
<212> TYPE: DNA
<213> ORGANISM: Artificial Sequence
<220> FEATURE:
<223> OTHER INFORMATION: PCR primer

<400> SEQUENCE: 4
cggagctggg tggccccatg catt                                       24

<210> SEQ ID NO 5
<211> LENGTH: 27
<212> TYPE: DNA
<213> ORGANISM: Artificial Sequence
<220> FEATURE:
<223> OTHER INFORMATION: PCR primer

<400> SEQUENCE: 5
cctgtgagga actactgtct tcacgca                                    27

<210> SEQ ID NO 6
<211> LENGTH: 27
<212> TYPE: DNA
<213> ORGANISM: Artificial Sequence
<220> FEATURE:
<223> OTHER INFORMATION: PCR primer

<400> SEQUENCE: 6
actcgcaagc accctatcag gcagtac                                    27

<210> SEQ ID NO 7
<211> LENGTH: 25
<212> TYPE: DNA
<213> ORGANISM: Artificial Sequence
<220> FEATURE:
<223> OTHER INFORMATION: PCR primer

<400> SEQUENCE: 7
```

| aagcgtctag ccatggcgtt agtat | 25 |

<210> SEQ ID NO 8
<211> LENGTH: 27
<212> TYPE: DNA
<213> ORGANISM: Artificial Sequence
<220> FEATURE:
<223> OTHER INFORMATION: PCR primer

<400> SEQUENCE: 8

| actcgcaagc accctatcag gcagtac | 27 |

<210> SEQ ID NO 9
<211> LENGTH: 20
<212> TYPE: DNA
<213> ORGANISM: Artificial Sequence
<220> FEATURE:
<223> OTHER INFORMATION: PCR primer

<400> SEQUENCE: 9

| cccattacat caggatccgg | 20 |

<210> SEQ ID NO 10
<211> LENGTH: 20
<212> TYPE: DNA
<213> ORGANISM: Artificial Sequence
<220> FEATURE:
<223> OTHER INFORMATION: PCR primer

<400> SEQUENCE: 10

| ttggtccgcc tcatcctcca | 20 |

<210> SEQ ID NO 11
<211> LENGTH: 20
<212> TYPE: DNA
<213> ORGANISM: Artificial Sequence
<220> FEATURE:
<223> OTHER INFORMATION: PCR primer

<400> SEQUENCE: 11

| ggtacctctt gatgcgaagg | 20 |

<210> SEQ ID NO 12
<211> LENGTH: 22
<212> TYPE: DNA
<213> ORGANISM: Artificial Sequence
<220> FEATURE:
<223> OTHER INFORMATION: PCR primer

<400> SEQUENCE: 12

| ggccacactt ttaaggagct ta | 22 |

<210> SEQ ID NO 13
<211> LENGTH: 20
<212> TYPE: DNA
<213> ORGANISM: Artificial Sequence
<220> FEATURE:
<223> OTHER INFORMATION: PCR primer

<400> SEQUENCE: 13

| cctgctggtg gctccagttc | 20 |

<210> SEQ ID NO 14
<211> LENGTH: 24
<212> TYPE: DNA
<213> ORGANISM: Artificial Sequence

```
<220> FEATURE:
<223> OTHER INFORMATION: PCR primer

<400> SEQUENCE: 14
tacccaaaga caaagaaaa ttgg                                              24

<210> SEQ ID NO 15
<211> LENGTH: 23
<212> TYPE: DNA
<213> ORGANISM: Artificial Sequence
<220> FEATURE:
<223> OTHER INFORMATION: PCR primer

<400> SEQUENCE: 15
tagtaaactg agccargaga aac                                              23

<210> SEQ ID NO 16
<211> LENGTH: 23
<212> TYPE: DNA
<213> ORGANISM: Artificial Sequence
<220> FEATURE:
<223> OTHER INFORMATION: PCR primer

<400> SEQUENCE: 16
gttgacaara atcctcacaa tac                                              23
```

METHOD FOR ISOLATING PROTEINS OR PROTEIN AND NUCLEIC ACID ASSOCIATIONS, OR PARTICLE AND PROTEIN COMPLEXES, REAGENT AND USES

This is a Division of application Ser. No. 10/182,126, filed Jan. 13, 2003 now U.S. Pat. No. 7,060,804, which is a National Stage of PCT/FR01/00205 filed Jan. 22, 2001, which claims priority to FR 00 00862 filed Jan. 21, 2000. The entire disclosure of the prior applications is hereby incorporated by reference herein in its entirety.

BACKGROUND

One of the problems which is repeatedly encountered concerns the extraction, purification, concentration and conservation of biological material for the purpose of subsequent use.

One of the protein purification methods used is purification by precipitation using precipitating agents, such as ammonium sulfate or poly(acrylic acids) (H. Morawetz and W. L. Hughes, J. Phys. Chem., 56, 64-69 (1952)).

Another method relates to the extraction of biological material using colloidal suspensions. Mention may be made of patent application WO-A-98/01482 by Krupey, which describes extraction of proteins in an aqueous medium using colloids based on crosslinked maleic anhydride copolymers. After complexation of the proteins on the colloids, the complexes are extracted from the medium by centrifugation. Such a method has the drawback of requiring a relatively delicate centrifugation step and involving considerable and expensive equipment which, in addition, is not always readily accessible.

A possible solution is to use magnetic iron oxide colloids, as described by V C Rao et al. (Appl. Environ. Microbiol., 1981, September, 42(3): 421-426). However, it is known that iron oxides are incompatible with techniques for enzymatically amplifying nucleic acids since they inhibit the enzymes.

To solve this problem, it has been proposed (patent application WO-A-99/35500) to cover magnetic particles with a cationic or anionic hydrophilic polymer, which masks the iron oxides and which thus makes it possible to lift the inhibition of the enzymatic amplification reaction, after a step of extraction of the nucleic acids. This polymer is a heat-sensitive polymer which, when it is heated to a temperature greater than 32° C., becomes hydrophobic and can attach proteins via hydrophobic interactions. However, hydrophobic interactions are denaturing for a large number of proteins.

SUMMARY

The present inventors have now found magnetic colloidal particles which overcome all the abovementioned drawbacks and which are also ubiquitous, in the sense that they allow the isolation of proteins and of protein and nucleic acid associations from a complex medium in a simple, effective and rapid manner which does not require expensive equipment, and which are compatible with enzymatic amplification techniques. They do not involve extensive equipment, nor many manipulations. Such particles can therefore be used independently of the environment in which they are located and allow, inter alia, the extraction of protein and nucleic acid associations, but also the extraction of proteins.

The term "proteins" is intended to mean holoproteins and heteroproteins, or fragments thereof, i.e. lipoproteins, glycoproteins, hemoproteins, phosphoproteins, flavoproteins, metalloproteins, polypeptides, antigens, immunogens, antibodies and enzymes.

The expression "protein and nucleic acid association" is in particular intended to mean complex nucleoprotein structures such as chromosomes or histones, and also viruses, bacteria and fungi.

Such particles are particularly advantageous in regions where hemorrhagic fever viruses are endemic.

In particular, the particles of the invention may be transported without a lyophilization step or a freezing step, which has unquestionable advantages, in particular in terms of safety when infectious samples are transported. A recent epidemic in the Congo showed the difficulties which may be encountered in the field, when samples of human origin which posed very considerable risks of contamination were transported to South Africa for diagnosis (World Health Organization, 1999).

In addition, the colloidal particles of the invention make it possible, if desired, to infect cells placed in culture, with an infectious agent thus isolated, purified, concentrated and, optionally, transported. Thus, there are many applications and uses for the colloidal particles of the invention.

In the case of viruses, for example, a step of lysis using chaotropic agents, heat or other means is essential prior to the enzymatic amplification phase, which requires the use of colloids which are stable under high stringency conditions. The method for preparing these stable colloids is incorporated into the examples of the present patent application by way of illustration.

Thus, the present invention relates to a method for isolating proteins and/or a protein and nucleic acid association, from a sample, characterized in that:

said sample is brought into contact with magnetic colloidal particles comprising a core and an envelope in which:

the core is magnetic and is coated with at least one polymer comprising functional groups X chosen from amine, hydroxyl, thiol, aldehyde, ester, anhydride, acid chloride, carbonate, carbamate, isocyanate and isothiocyanate groups, or mixtures thereof, at least one fraction of which has reacted with other functional groups of the envelope, and the envelope consists of a polymer bearing ionizable functional groups, Z and Z', which may be identical or different, chosen from amine, carboxylic acid, ester, anhydride, aldehyde, thiol, disulfide, α-halocarbonyl, sulfonic acid, maleimide, isocyanate and isothiocyanate groups, which have partially reacted with the fictional groups X of the core;

so as to constitute a mixture, said mixture is incubated under predetermined conditions, and the proteins and/or the protein and nucleic acid associations complexed on said colloidal particles are separated from the mixture by applying a magnetic field.

In particular, the magnetic core is solid and consists of metal oxide particles, or it consists of an emulsion comprising metal oxide particles, said metal oxide particles or said emulsion of metal oxide particles.

From "partial reaction of the functional groups Z, Z' with X", it is understood that groups Z and/or Z' must remain available. All or at least some of these free groups Z and/or Z' will react via ionic interaction with the ionic groups of the proteins and/or protein and nucleic acid associations.

Table 1 below summarizes the complementarity between the various functional groups X, Z and Z'.

TABLE 1

| X | Z | Z' |
|---|---|---|
| Ester, anhydride, acid chloride, carbonate, carbamate, isocyanate, isothiocyanate | Amine | Amine, thiol, carboxylic acid, ester, sulfonic acid |
| Aldehyde | Amine | Amine, thiol, carboxylic acid, ester, sulfonic acid |
| Amine, hydroxyl | Carboxylic acid, ester, anhydride, aldehyde, isocyanate, isothiocyanate | Carboxylic acid, sulfonic acid |
| Thiol | Thiol, disulfide, α-halocarbonyl maleimide | Amine, carboxylic acid, ester, anhydride, sulfonic acid |

The core of the colloidal particles comprises at least one organic polymer chosen from at least one homopolymer or one copolymer, or mixtures thereof, derived from the polymerization of at least one monomer chosen from monomers of acrylamide and of acrylate, in particular N-alkylacrylamides and N,N-dialkylacrylamides, such as N-isopropylacrylamide, N-methylacrylamide, N-ethylmethacrylamide, N-n-propylacrylamide, N-n-propylmethacrylamide, N-isopropylmethacrylamide, N-cyclopropylacrylamide, N,N-diethylacrylamide, N-methyl-N-isopropylacrylamide or N-methyl-N-n-propylacrylamide; alkylacrylates and alkylmethacrylates in which the alkyl group comprises from 3 to 20 carbon atoms; styrene, methylstyrene, ethylstyrene, tert-butylstyrene, chloromethylstyrene vinyltoluene; derivatives thereof and the copolymers of these monomers with one another and/or with other comonomers, and metal oxide particles chosen from particles of metal oxides of iron, titanium, cobalt, zinc, copper, manganese, nickel; magnetite; hematite, ferrites such as manganese, nickel or manganese-zinc ferrites; alloys of cobalt, nickel.

The envelope polymer is chosen from at least one hydrophilic homopolymer or copolymer chosen from homopolymers or copolymers:

derived from the polymerization of at least one monomer chosen from monomers derived from acrylamide or from methacrylamide; acrylic acid, methacrylic acid; acrylate and methacrylate derivatives; allylamine; styrene derivatives; on the condition, if it is a homopolymer, that this homopolymer comprises ionizable functional groups; in particular copolymers or homopolymers of maleic anhydride and homopolymers or copolymers of acryloxysuccinimide, polysaccharides, such as chitosan and poly(galacturonic acid), polypeptides, such as polylysine and polyarginine, linear or branched polyethyleneimine, and dendrimers;

preferably poly(maleic anhydride vinyl ether), poly(N-vinylmorpholine-N-acryloxysuccinimide) or poly(N-vinylpyrolidone-N-acryloxysuccinimide).

The mixture is subjected to incubation at a temperature of between 15 and 60° C., preferably between 20 and 35° C., for an incubation time of between 5 and 60 minutes, preferably 10 minutes.

The sample may be a biological sample, for example a specimen, such as a tissue specimen, a specimen of whole blood or of serum or a culture supernatant, or alternatively an agrofoods specimen, comprising proteins and/or protein and nucleic acid associations, in particular a virus, a bacterium, a yeast and/or a cell, optionally as a mixture. The "agrofoods specimen" is intended to mean any agrofoods sample liable to be, or to have been, infected with an infectious agent.

The invention also relates to a method for extracting proteins and/or a protein and nucleic acid association, according to which a virus and/or a bacterium and/or a yeast and/or a cell or a mixture thereof is isolated from a sample, for example an agrofoods specimen or a biological sample such as a specimen or a culture supernatant, according to the method described above and, if necessary, said virus, bacterium, yeast, cell or mixture thereof is subjected to a step of partial or total release and/or denaturation for the extraction of said proteins and/or said nucleic acids.

The invention also relates to a method for identifying and/or detecting and/or quantifying proteins and/or a protein and nucleic acid association and/or nucleic acids, according to which a virus and/or a bacterium and/or a yeast and/or a cell or a mixture thereof is isolated from a sample, for example from a specimen or from a culture supernatant, according to the method described above, if necessary said virus and/or bacterium and/or yeast and/or cell or mixture thereof is subjected to a step of partial or total release and/or denaturation for the extraction of said proteins and/or said nucleic acids, and said proteins are identified and/or detected and/or quantified by immunoassay and/or said nucleic acids are identified and/or detected and/or quantified by amplifying them and/or by hybridization of at least one nucleotide probe specific for said nucleic acids to be identified and/or detected and/or quantified.

The term "immunoassay" is intended to mean the detection and/or quantification of at least one protein or of at least one antigen by revelation of a protein or antigen/antibody complex, in particular using "Western blotting", "competition" or "sandwich" techniques.

The term "amplification" is intended to mean all techniques suitable for amplifying DNA or RNA, in particular PCR, RT-PCR, NASBA, and TMA. It may involve, inter alia, a quantitative amplification. Moreover, the nucleic acids to be identified and/or detected and/or quantified may be so by hybridization of at least one nucleotide probe labeled with any suitable label, preferably by hybridization of the target to a capture probe and to a detection probe. By way of nonlimiting example, mention may be made of the techniques, which are well known to those skilled in the art, of Southern blotting and of Northern blotting and of the ELOSA (Enzyme Linked Oligosorbent Assay) technique (Katz J B et al., Am. J. Vet. Res., 1993 December; 54 (12): 2021-6 and Francois Mallet et al., Journal of Clinical Microbiology, June 1993, p. 1444-1449).

The proteins are surface or intracellular proteins of a virus, of a bacterium, of a yeast or of a cell, and the nucleic acids are DNA and/or RNA. The proteins are identified and/or detected and/or quantified (i) either directly, without a step of release and/or denaturation, from said virus and/or bacterium and/or yeast and/or cell, isolated or in a culture supernatant, (ii) or indirectly, after a step of partial or total release and/or denaturation carried out, for example, by modification of pH (decrease or increase in pH by addition of an acid or basic solution). The nucleic acids are identified and/or detected and/or quantified after a step of partial or total release and/or denaturation of said isolated virus and/or bacterium and/or yeast and/or cell carried out, for example, by chemical and/or physical treatment. By way of example, a chemical treatment includes the use of surfactants, such as SDS or LLS, the use of chaotropic agents, such as guanidium thiocyanate, and the use of enzymes, such as proteases (proteinase K), or other suitable agents. By way of example, a physical treatment comprises sonication, heating, ultrasound, mechanical agitation (with, for example, rigid beads of the glass type) or the like.

The invention also relates to a method for culturing a virus and/or a bacterium and/or a yeast and/or cells, according to which said virus and/or said bacterium and/or said yeast and/or said cells are isolated from a sample, for example a specimen or a culture supernatant, according to the method described above, said virus and/or bacterium and/or yeast and/or cells thus isolated are placed in culture, in a culture medium and under conditions which are suitable, and, if desired, said virus and/or bacterium and/or yeast and/or cells are identified and/or detected and/or quantified according to techniques well known to those skilled in the art.

Another subject of the invention is a method for preparing a biological sample, such as a specimen or a culture supernatant, or an agrofoods specimen, according to which proteins and/or protein and nucleic acid associations are isolated from the sample, according to the method above, and/or a culture is prepared according to a method as described above.

The invention also relates to a complex made up of magnetic colloidal particles and proteins and/or a protein and nucleic acid association, the proteins and nucleic acids being immobilized by electrostatic interactions and/or by adsorption. The colloidal particles comprise a core and an envelope in which:

the core is magnetic and is coated with at least one polymer comprising functional groups X chosen from amine, hydroxyl, thiol, aldehyde, ester, anhydride, acid chloride, carbonate, carbamate, isocyanate and isothiocyanate groups, or mixtures thereof, at least one fraction of which has reacted with other functional groups of the envelope, and the envelope consists of a polymer bearing ionizable functional groups, Z and Z', which may be identical or different, chosen from amine, carboxylic acid, ester, anhydride, aldehyde, thiol, disulfide, α-halocarbonyl, sulfonic acid, maleimide, isocyanate and isothiocyanate groups, at least some of which have reacted with the functional groups X of the core; and the proteins and/or protein and nucleic acid associations are derived from a biological sample, for example from a specimen, such as a tissue specimen or a specimen of whole blood or of serum, or from a culture supernatant, or from an agrofoods specimen.

In particular, the core of the colloidal particles is solid and consists of metal oxide particles, or is essentially solid and consists of an emulsion comprising metal oxide particles.

Preferably, the specimen or the culture supernatant is infected with at least one virus, one bacterium or one yeast, or a mixture thereof.

The core comprises at least one organic polymer chosen from at least one homopolymer or one copolymer, or mixtures thereof, derived from the polymerization of at least one monomer chosen from monomers of acrylamide and of acrylate, in particular N-alkylacrylamides and N,N-dialkylacrylamides, such as N-isopropylacrylamide, N-methylacrylamide, N-ethylmethacrylamide, N-n-propylacrylamide, N-n-propylmethacrylamide, N-isopropylmethacrylamide, N-cyclopropylacrylamide, N,N-diethylacrylamide, N-methyl-N-isopropylacrylamide or N-methyl-N-n-propylacrylamide; alkylacrylates and alkylmethacrylates in which the alkyl group comprises from 3 to 20 carbon atoms; styrene, methylstyrene, ethylstyrene, tert-butylstyrene, chloromethylstyrene vinyltoluene; derivatives thereof and the copolymers of these monomers with one another and/or with other comonomers, and metal oxide particles chosen from particles of metal oxides of iron, titanium, cobalt, zinc, copper, manganese, nickel; magnetite; hematite, ferrites such as manganese, nickel or manganese-zinc ferrites; alloys of cobalt, nickel.

The envelope polymer is chosen from at least one hydrophilic homopolymer or copolymer chosen from homopolymers or copolymers:

derived from the polymerization of at least one monomer chosen from monomers derived from acrylamide or from methacrylamide; acrylic acid, methacrylic acid; acrylate and methacrylate derivatives; allylamine; styrene derivatives; on the condition, if it is a homopolymer, that this homopolymer comprises ionizable functional groups; in particular copolymers or homopolymers of maleic anhydride and homopolymers or copolymers of acryloxysuccinimide, polysaccharides, such as chitosan and poly(galacturonic acid), polypeptides, such as polylysine and polyarginine, linear or branched polyethyleneimine, and dendrimers;

in particular poly(maleic anhydride vinyl ether), poly(N-vinylmorpholine-N-acryloxysuccinimide) or poly(N-vinylpyrrolidone-N-acryloxysuccinimide).

This complex is used for the transfer and/or transport and/or storage of infectious agents, in particular of a virus and/or bacterium and/or yeast, in the dry state or in a suitable buffer.

The invention also relates to a reagent for extracting and/or identifying and/or detecting and/or quantifying proteins and/or protein and nucleic acid associations, characterized in that it comprises, inter alia:

a complex as defined above, or colloidal particles as defined above which make it possible to obtain a complex of the invention, and optionally at least one means for identifying and/or detecting and/or quantifying said proteins or said nucleic acids, in particular at least one monoclonal or polyclonal antibody for identifying and/or detecting and/or quantifying at least one protein, and at least one primer, preferably at least two primers, and/or at least one nucleotide probe, preferably at least two nucleotide probes, specific for at least one nucleic acid, for the identification and/or detection and/or quantification thereof.

Finally, the invention relates to a vaccinal composition which comprises, as active principle, at least one complex of the invention as defined above, optionally combined with a pharmaceutically acceptable vehicle and/or excipient and/or adjuvant and/or diluent.

The term "pharmaceutically acceptable vehicle" is intended to mean the carriers and vehicles which can be administered to humans or to animals, as described, for example, in Remington's Pharmaceutical Sciences 16th ed., Mack Publishing Co. The pharmaceutically acceptable vehicle is preferably isotonic or hypotonic or is weakly hypertonic and has a relatively low ionic strength. The definitions of the pharmaceutically acceptable excipients and adjuvants are also given in Remington's Pharmaceutical Sciences, mentioned above.

Another subject of the invention is a pharmaceutically acceptable vehicle for a vaccinal composition, consisting of a magnetic particle corresponding to the definition of the present invention.

DETAILED DESCRIPTION OF EMBODIMENTS

Example 1

Production of Carboxylic Magnetic Latexes

The polymer poly(maleic anhydride methyl vinyl ether) (MAMVE) is solubilized in anhydrous dimethyl sulfoxide (DMSO) (2 g/l). 50 µl of this MAMVE solution are diluted in 1 ml of phosphate buffer (pH 6.8; 10 mM) and then incubated for 10 minutes at 37° C. 1 ml of a dispersion of aminated magnetic latex (0.5% in water, 1× the critical micellar concentration (CMC) of Triton X-405) produced, for example, according to the protocol described in patent application PCT WO 99/35500, is then mixed with 125 µl of the previously prepared mixture (MAMVE-DMSO-buffer). The mixture is incubated at 37° C. for 3 hours. The particles can then be solubilized as they are or after a purification step, for example by centrifugation.

Example 2

Selective Extraction of Viral Particles from Serum, from Plasma or from Culture Supernatants Purification of Viral Particles:

From 100 to 150 µl of positive serum, i.e. serum comprising viral particles, are added directly to 5 µl of magnetic latex functionalized with the MAMVE copolymer, as described in Example 1, at a solids content of 3%. The sample is not buffered.

The serum-latex mixture is homogenized on a vortex for 10 seconds and then left at ambient temperature for 10 minutes in order for the magnetic latex to attach the viral particles. This capture step is followed by recovery of the latex-viral particle complex, in the form of a pellet from which the supernatant has been removed, by simple magnetization for 30 seconds.

The pellet may or may not be washed once with 100 µl of Hepes, pH 6.5, magnetized as previously and then dispersed in 50 µl of sterile water.

Extraction of Nucleic Acids after Heat-Lysis of Viral Particles:

The latex-viral particle complex dispersed in water is incubated at 95° C. for 5 minutes in order to lyse the viral particles. The nucleic acids are recovered from the supernatant from which the latex has been removed by magnetization.

Example 3

Capture of the Hepatitis G Virus Using a Functionalized Magnetic Latex of the Invention Purification of Viral Particles:

Increasing volumes, respectively of 25 µl and 50 µl, of undiluted human serum positive for the hepatitis G virus, the viral titer of which is unknown, are added to 5 µl of the magnetic latex functionalized with the MAMVE copolymer, as described in Example 1, at a solids content of 3%.

The serum-latex mixture is homogenized on a vortex for 10 seconds and then left at ambient temperature for 10 minutes in order for the magnetic latex to attach the viral particles. This capture step is followed by recovery of the latex-viral particle complex, in the form of a pellet from which the supernatant has been removed, by simple magnetization for 5 minutes.

The pellet is then washed once with 50 µl of Hepes-Tween (0.25/∞, pH 6.5), magnetized as previously, and then dispersed in 50 µl of sterile water.

Extraction of Nucleic Acids:

A step of viral particle lysis is then carried out using the QIAmp Viral RNA Mini Kit (commercial name), marketed by the company QIAGEN, so as to release the viral nucleic acids.

Amplification of Nucleic Acids:

The viral nucleic acids are then amplified by one-step RT-PCR (1) (Life Technologies) and nested PCR (2) using the following pairs of primers (Smith D B et al., Discrimination of hepatitis G virus/GBV-C geographical variants by analysis of the 5' non-coding region, J. Gen. Virol., 1997, 78: 1533-1542):

```
(1): primer 1: 5' AGG TGT GGA TGG GTG ATG 3'         (SEQ ID NO: 1)
     primer 2: 5' ATG CCA CCC GCC CTC ACC CGA 3'     (SEQ ID NO: 2)

(2): primer 1: 5' TTG GTA GGT CGT AAA TCC CGG 3'     (SEQ ID NO: 3)
     primer 2: 5' CGG AGC TGG GTG GCC CCA TGC ATT 3'. (SEQ ID NO: 4)
```

The results, after running on a 1% agarose gel and staining with ethidium bromide, show a band of expected size of 343 base pairs, after the second PCR. The molecular weight marker used as reference is the Smartladder marker (commercial name) (multiples of 200 base pairs) from the company Eurogentec. These results confirm that the functionalized latex of the invention is capable of capturing the hepatitis G viral particles and of retaining them during the washing steps.

Moreover, 10 µl of human serum positive for HGV, of unknown titer, were diluted in 3 ml of negative human serum and brought into contact with 10 µl of the latex of the invention, obtained according to Example 1. The viral particle purification, nucleic acid extraction and amplification steps were carried out as described above.

The results obtained show, after running the amplification products on 1% agarose gel and staining with ethidium bromide, the band of expected size of 343 base pairs, which confirms the ability of the latex of the invention to capture and retain the viral particles from a diluted sample of large volume.

Example 4

Capture of the Hepatitis C Virus with a Functionalized Magnetic Latex of the Invention Purification of Viral Particles:

50 µl volumes of an undiluted human serum positive for the hepatitis C virus, the viral titer of which is unknown, are added to 5 µl of the magnetic latex functionalized with the MAMVE copolymer, as described in Example 1, at a solids content of 3%.

The serum-latex mixture is homogenized on a vortex for 10 seconds and then left at ambient temperature for 10 minutes in order for the magnetic latex to attach the viral particles. This capture step is followed by recovery of the latex-viral particle complex, in the form of a pellet from which the supernatant has been removed, by simple magnetization for 5 minutes.

The pellet is then washed once with 50 µl of Hepes-Tween (0.25/∞, pH 6.5), magnetized as previously, and then dispersed in 50 µl of sterile water.

Extraction of Nucleic Acids:

A step of nucleic acid extraction is then carried out using the QIAmp Viral RNA Mini Kit (commercial name), marketed by the company QIAGEN, so as to release the viral nucleic acids.

Amplification of Nucleic Acids:

The viral nucleic acids are then amplified by one-step RT-PCR (1) (Life Technologies), followed by a semi-nested PCR (2) using the following pairs of primers (Li J S et al., Identification of the third major genotype of hepatitis C in France, BBRC, 1994, 3: 1474-1481):

```
(1): primer 1: 5' CCT GTG AGG AAC TAC TGT CTT CAC GCA 3'   (SEQ ID NO: 5)
     primer 2: 5' ACT CGC AAG CAC CCT ATC AGG CAG TAC 3'   (SEQ ID NO: 6)

(2): primer 1: 5' AAG CGT CTA GCC ATG GCG TTA GTA T 3'     (SEQ ID NO: 7)
     primer 2: 5' ACT CGC AAG CAC CCT ATC AGG CAG TAC 3'.  (SEQ ID NO: 8)
```

The results, after running on a 1% agarose gel and staining with ethidium bromide, show a band of expected size of 240 base pairs, after the second PCR. The molecular weight marker used as reference is the Smartladder marker (commercial name) (multiples of 200 base pairs) from the company Eurogentec. These results confirm that the functionalized latex of the invention is capable of capturing the hepatitis G viral particles and of retaining them during the washing steps.

Example 5

Detection of the Measles Virus

The nucleic acids were extracted from previously titered viral samples using the kit marketed by the company QIAGEN (QIAmp Viral RNA Mini Kit (commercial name)), according to the supplier's protocol. The nucleic acids were then amplified by RT-PCR using the TITAN kit (commercial name—Roche) in the presence of 1 µl of RNAase inhibitor (RNAsin, commercial name—Promega) or by nested PCR.

Titering of viral samples (Edmonston strain): successive dilutions of the virus were prepared (from $10^{-1}$ to $10^{-7}$). 200 µl of these dilutions were distributed into the 6 wells of a plate containing Vero cells (green monkey kidney cells) cultured in a medium 199 containing glutamax (Gibco-BRL), 1% of antibiotics (Gibco-BRL) and 1% of fetal calf serum. The Vero cells are 80% confluent. Incubation was carried out for one hour at 37° C. under $CO_2$ (5%). 200 µl of the medium containing the virus were removed and replaced with 200 µl of virus-free medium. Incubation was carried out under the same conditions for 72 to 96 hours. The cells are then examined and the lysis plaques are visualized and counted. 60 ml of culture with a titer of 5.5 $10^6$ pfu/ml (lysis plaque forming unit/ml) were obtained, aliquoted and stored at −80° C.

Extraction of nucleic acids: the nucleic acids are extracted from the culture (5.5 $10^3$ pfu/µl) using the above-mentioned kit from the company QIAGEN.

Amplifications: the extracted nucleic acids are amplified by RT-PCR using the following pair of PCR primers:

```
primer 1:
5' CCC ATT ACA TCA GGA TCC GG 3'    (SEQ ID NO: 9)

primer 2:
5' TTG GTC CGC CTC ATC CTC CA 3'    (SEQ ID NO: 10)
``` optionally followed by a nested PCR using the following pair of primers:

```
primer 1: 5' GGT ACC TCT TGA TGC GAA GG 3'    (SEQ ID NO: 11)
primer 2: 5' GGC CAC ACT TTT AAG GAG CTT A 3'. (SEQ ID NO: 12)
```

The amplification products are then run on 2% agarose gel (TBE+Gelstar). The molecular weight marker used as reference is the Smartladder marker (commercial name) (multiples of 100 base pairs) from the company Eurogentec. The results show a band of expected size of 384 base pairs for the RT-PCR and of 309 base pairs for the nested PCR, which confirms the correct extraction of the viral RNAs and the efficiency of both the RT-PCR and the nested PCR.

Example 6

Capture of the Measles Virus Using the Functionalized Latex of the Invention

After obtaining titered viral samples, as described in Example 8, the level of viral capture and detection using the latex of Example 1 was quantitatively determined. A range of viral titers was produced by diluting the stock solution in negative human plasma. 10-fold dilutions were made in a final volume of 1000 µl. The amount of latex is 35 µl (945 µg) per sample. After capture, the viral RNAs are extracted using the abovementioned QIAGEN kit. The extracted viral RNAs are then amplified by RT-PCR followed by a nested PCR using the pairs of primers described in Example 5. The amplification products are then run on a 2% agarose gel (TBE+Gelstar). A molecular weight marker (multiple of 200 base pairs) (Smartladder–Eurogentec) is used as reference. The positive control is represented by the extracted total RNA and the negative control consists of negative plasma. The results are given in Table 2 below.

TABLE 2

| Negative control Negative plasma | Positive control Total RNA | Dilutions in pfu (lysis plaque forming unit) | | | | | | | |
|---|---|---|---|---|---|---|---|---|---|
| | | $10^6$ | $10^5$ | $10^4$ | $10^3$ | $10^2$ | 10 | 1 | $10^{-1}$ |
| − | + | + | + | + | + | + | + | + | − |

The symbol + signifies the presence of the amplification product of expected size (309 base pairs) and the symbol − signifies an absence of amplification product.

The results show that the nested PCR gives a specific amplification product down to 1 pfu per tube (100 µl). The absence of amplification product at the 0.1 pfu dilution indicates that there is no detection of noninfectious viral particles.

Example 7

Study of the Stability of the Latex/Measles Virus Complex

In order to study the stability of the latex/virus complexes, relative to the detection of the viral RNAs by RT-PCR, the complexes were revealed over time. Several infectious titers were tested, as were different treatments of the samples, with the aim of preserving the samples while at the same time reducing the number of manipulations. The samples were kept under a laminar flow hood, at ambient temperature.

The complexes, having undergone treatments or not having undergone treatments, were tested on day 0, 1, 2, 3, 7 and 14, respectively:

Treatment A: sample of plasma containing the virus and the latex, which serves as a basic control (no treatment).

Treatment B: latex/virus complex, after removal of the plasma, no washing and left dry.

Treatment C: latex/virus complex, after removal of the plasma and a washing step and left dry.

Treatment D: latex/virus complex, after removal of the plasma and a washing step and kept in the presence of washing buffer.

The infectious titers of the samples tested are, respectively, 50, 500 and 5000 pfu per sample for each treatment.

The complexes are then heat-lysed so as to release the nucleic acids, and the nucleic acids are run on 2% agarose gels (TBE+Gelstar) with a molecular weight marker used as reference (Smartladder−Eurogentec).

The results, under the conditions of the experiment, show that treatment B does not make it possible to conserve the viral particles in a stable manner. However, it should be noted that, if a washing step is carried out before the nucleic acid extraction step, the latex of the invention conserves the particles in a stable manner, as shown by the inventors in another experiment. On the other hand, complexes C and D, which undergo a washing step, make it possible to conserve the samples without the RNAs being degraded, as demonstrated by RT-PCR. This means that a step consisting of washing in a buffer is necessary in order to conserve the captured sample, whether the latter is conserved in the buffer or dry, if the intention is to carry out the lysis step in the extraction tube, but a means of avoiding this washing step is to change tube. Of course, it is more advantageous to conserve the captured samples dry, since this makes it possible to transport them from the place where they are taken to a site for analysis while avoiding any risk of contamination and of dissemination.

Example 8

Capture of the Measles Virus from whole Blood

Tests were carried out using whole blood. A range of virus was established, in whole human blood and plasma of the same origin, with an equal amount of latex. The latex/viral particle complexes were subjected to heat treatment in order to extract the nucleic acids. The nucleic acids released were amplified by RT-PCR using the primers previously described.

The results obtained after running the amplification products on 2% agarose gel (TBE+Gelstar) show a band of expected size of 384 base pairs starting from a viral titer of 5 $10^3$ pfu in the whole blood and from 50 pfu in the plasma. These results show that it is possible to isolate viral particles from whole blood, although this is substantially less efficient than from plasma. The results are summarized in Table 3 below.

TABLE 3

| Sample | Infectious titer in pfu 0 | 10 | 50 | 500 | 5000 | 50 000 |
|---|---|---|---|---|---|---|
| Blood | − | − | − | − | + | + |
| Plasma | − | − | + | + | + | + |

Example 9

Culturing of Captured Measles Viruses

Using human plasma, a viral range was established and tested as described in Example 8 (see Table 2). The magnetic latex/measles virus complexes were placed in culture in the presence of Vero cells cultured in a medium 199 containing glutamax (Gibco-BRL), 1% of antibiotics (GIBCO-BRL) and 10% of fetal calf serum. The culturing conditions were established as described in Example 5. An RT-PCR was carried out on the viral range, the very day on which it was placed in culture, so as to validate the presence of the virus in the sample placed in culture. The cells of the culture were then observed under a microscope so as to detect a cytopathic effect induced by the infectious virus in the culture. A cytopathic effect was observed at the end of the third day for the samples for which the infectious titer was 5 $10^4$ and 5 $10^3$ pfu/ml, and after 5 days for the samples for which the infectious titer was 500 and 50 pfu/ml.

Example 10

Capture of the Acquired Immunodeficiency Syndrome Virus (HIV-1) Using the Functionalized Latex of the Invention, from a Culture Supernatant, and Study of the Viral Viability Viral Capture:

An HIV-1 viral strain of group M, subtype G was cultured in the presence of PBMCs (peripheral blood mononuclear cells) in an RPMI culture medium supplemented with 10% of fetal calf serum. The presence of the virus was confirmed on the 14th day of culturing by detection of the P24 antigen (31637.8 pg/ml, dilution to 1/100) in the culture supernatant using the VIDAS HIV P24 II immunoenzymatic test carried out on the VIDAS machine (registered trademark—bioMérieux). 150 µl of this culture supernatant were brought into contact with 10 µl of magnetic latex, obtained as described in Example 1, for 10 minutes at ambient temperature and with stirring. The capture step was followed by a magnetization step in order to separate the pellet from the culture supernatant, and the pellet thus obtained (latex-virus complex) was washed with approximately 100 µl of RPMI culture medium, and then magnetized again and resuspended in 10 µl of RPMI medium.

Viability:

10 µl of the latex-virus complex prepared as described above were brought into contact with a pellet of PBMCs (25 $10^6$ cells), freshly prepared. The mixture was homogenized and then subjected to incubation at 37° C. for two hours, for the PBMC infection step, under an atmosphere of $CO_2$ (5%). 15 ml of RPMI medium were then added. The mixture was homogenized and 5 ml of medium were removed on D0 and centrifuged at 1100 rpm for 10 minutes. 1 ml of supernatant will be used to assay the P24 and the remainder is returned to the corresponding culture medium. In parallel, freshly prepared PBMCs were placed in culture, under the same conditions, in the presence of 10 µl of latex alone (without virus) so as to constitute the negative control. The P24 antigen is assayed, using the immunoenzymatic test (VIDAS HIV P24 II) on the VIDAS machine, in the control and infected culture supernatant, respectively on days D0, D2, D4, D7, D9, D11, D14, D16 and D18. The results obtained show a significant increase in the P24 antigen in the culture supernatant from the 14th day of culturing, which confirms, firstly, that the virus has indeed been captured by the latex of the invention and that, secondly, it conserves, after capture, its viability and its replicative power (infectiousness).

Example 11

Capture of the Hepatitis B Virus (HBV)

Ten-fold dilutions of an HBV-positive serum were made, in a final volume of 150 µl, containing 10 000 to 10 viral copies. The viral capture and the viral DNA extraction were carried out according to the protocol described in Example 2.

The number of viral copies was detected by nested PCR using primers defined in the S region of the HBV genome for the amplification of a 440 base pair fragment.

1st Round:

```
Primer 1: 5' CCT GCT GGT GGC TCC AGT TC 3'         (SEQ ID NO: 13)
Primer 2: 5' TAC CCA AAG ACA AAA GAA AAT TGG 3'.   (SEQ ID NO: 14)
```

2nd Round:

```
Primer 3: 5' TAG TAA ACT GAG CCA RGA GAA AC 3'     (SEQ ID NO: 15)
Primer 4: 5' GTT GAC AAR AAT CCT CAC AAT AC 3'.    (SEQ ID NO: 16)
```

The amplification products are then run on a 1% agarose gel and stained with ethidium bromide. A signal is detected at the $10^{-3}$ dilution corresponding to a detection threshold of 10 HBV copies, representative of good sensitivity of the capture system of the invention.

Moreover, a positive human serum was diluted in negative human serum so as to obtain 100 copies of HBV in two different volumes of 100 and 1000 µl, in order to study a potential effect of concentration of the latex of the invention. After capture of the viral particles, contained in the two diluted samples, using 10 µl of latex, the nucleic acids were extracted by heat lysis and amplified by nested PCR using the primers described above. The amplification products are then run on 1% agarose gel and stained with ethidium bromide. The results show, for the products amplified from the two diluted samples, a band at the expected size of 440 base pairs. The intensity of staining of the two fragments amplified, derived, respectively, from the abovementioned two diluted samples, proves to be identical, which proves an effect of concentration of the magnetic latex of the invention.

What is claimed is:

1. A method for detecting a protein or a nucleic acid from a complex sample comprising a virus, prokaryotic cell or eukaryotic cell, the method comprising:
   (a) contacting the complex sample with magnetic colloidal particles to form a mixture, said magnetic colloidal particles comprising a core and an envelope, wherein:
      the core is magnetic and is coated with an organic polymer; said organic polymer is a homopolymer or copolymer of monomers selected from the group consisting of acrylamide, acrylate, styrene, methyistyrene, ethyistyrene, tert-butyl-styrene, chloromethylstyrene, and vinyltoluene;
      the organic polymer comprises functional groups selected from the group consisting of amine, hydroxyl, thiol, aldehyde, ester, anhydride, acid chloride, carbonate, carbamate, isocyanate, isothiocyanate groups, and mixtures thereof; and
      at least a fraction of the functional groups reacts with other functional groups of the envelope; and
   wherein:
      the envelope comprises a polymer that is a hydrophilic homopolymer or copolymer of monomers selected from the group consisting of acrylamide, methacrylamide, acrylic acid, methacrylic acid, allylamine, and styrene;
      if the polymer is a homopolymer, then the homopolymer comprises at least one member selected from the group consisting of polysaccharides, polypeptides, linear or branched polyethyleneimine, and dendrimers;
      the hydrophilic homopolymer or copolymer comprises ionizable functional groups that are identical or different;
      the ionizable functional groups are selected from the group consisting of amine, carboxylic acid, ester, anhydride, aldehyde, thiol, disulfide, α-halocarbonyl, sulfonic acid, maleimide, isocyanate, and isothiocyanate groups; and
      the ionizable functional groups partially react with the functional groups of the core;
   (b) homogenizing the mixture;
   (c) complexing said magnetic colloidal particles with said virus, prokaryotic cell, or eukaryotic cell;
   (d) applying a magnetic field to separate from the mixture said virus, prokaryotic cell or eukaryotic cell complexed on said magnetic colloidal particles; and
   (e) detecting said protein by an immunoassay or detecting said nucleic acid by hybridization.

2. The method of claim 1, wherein the protein is a surface or intracellular protein and the nucleic acid is a DNA or RNA.

3. The method of claim 1, further comprising:
   lysing said virus, prokaryotic cell or eukaryotic cell before step (e).

4. The method of claim 1, wherein said complex sample is a specimen or culture supernatant.

5. The method of claim 1, wherein step (e) is performed by detecting said protein by said immunoassay.

6. The method of claim 1, wherein step (e) is performed by detecting said nucleic acid by hybridization.

* * * * *